(12) United States Patent
Dauster et al.

(10) Patent No.: US 8,540,718 B2
(45) Date of Patent: Sep. 24, 2013

(54) ROD PERSUADER

(75) Inventors: Andrew Dauster, Whitehall, PA (US); Matthew Kovach, Steamboat Springs, CO (US); Paul Weaver, Douglassville, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 1527 days.

(21) Appl. No.: 11/975,922

(22) Filed: Oct. 23, 2007

(65) Prior Publication Data

US 2009/0105712 A1   Apr. 23, 2009

(51) Int. Cl.
*A61B 17/70* (2006.01)

(52) U.S. Cl.
USPC ........................................ 606/86 A

(58) Field of Classification Search
USPC ................. 606/86 A, 86 B, 99, 100
See application file for complete search history.

(56) References Cited

U.S. PATENT DOCUMENTS

| | | | |
|---|---|---|---|
| 5,720,751 A | 2/1998 | Jackson | |
| 5,782,830 A | 7/1998 | Farris | |
| 5,911,722 A | 6/1999 | Adler | |
| 5,928,244 A | 7/1999 | Tovey | |
| 5,935,133 A | 8/1999 | Jones | |
| 6,110,179 A | 8/2000 | Flivik | |
| 6,139,551 A | 10/2000 | Michelson | |
| 6,183,472 B1 | 2/2001 | Lutz | |
| 6,440,133 B1 | 8/2002 | Beale | |
| 6,660,006 B2 | 12/2003 | Markworth | |
| 6,682,533 B1 | 1/2004 | Dinsdale | |
| 6,746,449 B2 | 6/2004 | Jones | |
| 6,790,209 B2 | 9/2004 | Beale | |
| 2004/0147937 A1 | 7/2004 | Dunbar | |
| 2004/0254576 A1 | 12/2004 | Dunbar | |
| 2005/0004573 A1 | 1/2005 | Abdou | |
| 2005/0131419 A1 | 6/2005 | McCord | |
| 2005/0131420 A1 | 6/2005 | Techiera | |
| 2005/0149048 A1 | 7/2005 | Leport | |
| 2005/0192587 A1 | 9/2005 | Lim | |
| 2005/0228392 A1 | 10/2005 | Keyer | |
| 2006/0036254 A1 | 2/2006 | Li | |
| 2006/0036260 A1 | 2/2006 | Runco | |
| 2006/0074418 A1* | 4/2006 | Jackson | 606/61 |
| 2006/0106394 A1 | 5/2006 | Colleran | |

* cited by examiner

*Primary Examiner* — Eduardo C Robert
*Assistant Examiner* — Julianna N Harvey
(74) *Attorney, Agent, or Firm* — RatnerPrestia

(57) ABSTRACT

A rod persuader assembly includes a tubular body, an inner shaft and an outer shaft. The inner shaft is axially displaceable relative to the tubular body, and has a gripping end and a handle end. The outer shaft is axially displaceable relative to the tubular body, and has a rod reducing end. In one embodiment, the handle end is rotatable relative to the gripping end. In another embodiment, the gripping end includes a cylindrical socket. In yet another embodiment, the rod persuader assembly is operable in two separate and independent stages to secure the instrument to an implant, and advance a rod into the implant.

23 Claims, 16 Drawing Sheets

ROD PERSUADER

FIELD OF THE INVENTION

The present invention relates generally to spinal fixation systems and more specifically to instruments for positioning and securing spinal fixation rods to screw and hook implants.

BACKGROUND OF THE INVENTION

A number of pedicle screw systems in the state of the art include a screw or hook implant attached to a body for receiving a spinal rod. The body typically includes a channel for receiving and seating the rod. A locking element, such as a set screw, is inserted into the channel to lock the rod in place in the rod receiving body. Many times, rod reduction is necessary prior to inserting the locking element into the body to position and hold the rod against the seat.

Rod persuader instruments that are used to perform rod reduction must apply sufficient force to position the rod in the body of the pedicle screw or hook. Some rod persuader instruments are actuated by articulating handles that extend laterally from the main shaft of the instrument. This can add undesired weight to the instrument and create a visual obstruction over the implant site. Other rod persuader instruments require constant force to be applied manually on the actuator to hold the rod in the seated position while the set screw is manipulated. This limits the use of one hand when the set screw is being inserted and tightened into place.

In view of the foregoing, many known rod persuader instruments leave much to be desired in terms of ergonomics and functionality.

SUMMARY OF THE INVENTION

The drawbacks of rod persuader instruments known in the art are resolved in several respects by a rod persuader assembly in accordance with the present invention.

In a first aspect of the invention, a rod persuader assembly includes a tubular body, an inner shaft and an outer shaft. The inner shaft is axially displaceable relative to the tubular body, and has a gripping end and a handle end. The handle end is rotatable relative to the gripping end. The outer shaft is axially displaceable relative to the tubular body, and has a rod reducing end.

In a second aspect of the invention, a rod persuader assembly includes a tubular body, an inner shaft and an outer shaft. The inner shaft is axially displaceable relative to the tubular body, and has a gripping end and a handle end. The gripping end includes a cylindrical socket. The outer shaft is axially displaceable relative to the tubular body, and has a rod reducing end.

BRIEF DESCRIPTION OF THE DRAWINGS

The foregoing summary and following description will be better understood with reference to the non-limiting exemplary embodiments shown in the drawing figures, of which.

DETAILED DESCRIPTION OF THE INVENTION

Figure 1:
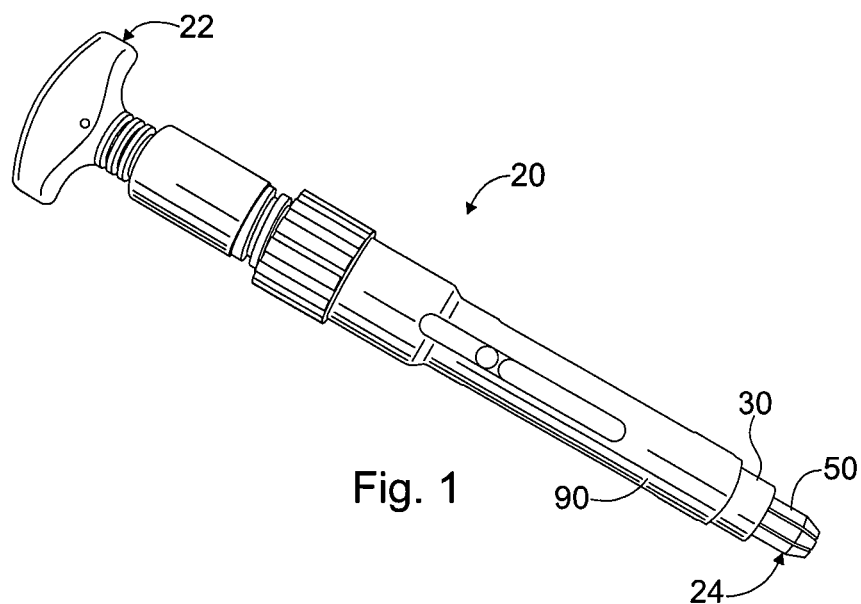
FIG. 1 is a first perspective view of an exemplary embodiment of a rod persuader in accordance with the present invention.
Figure 2:
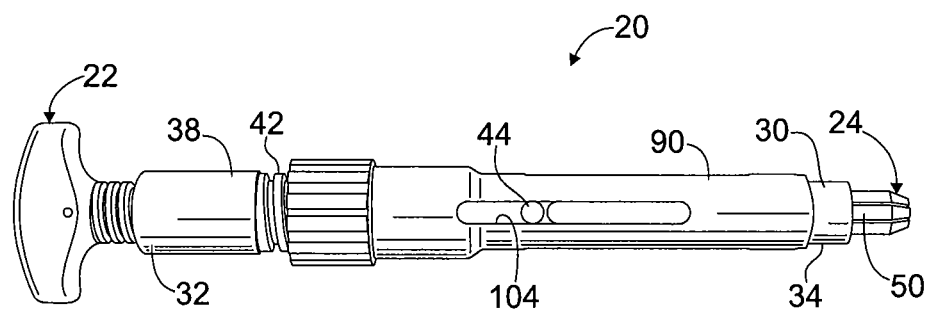
FIG. 2 is a first elevation view of the rod persuader embodiment of FIG. 1.
Figure 3:
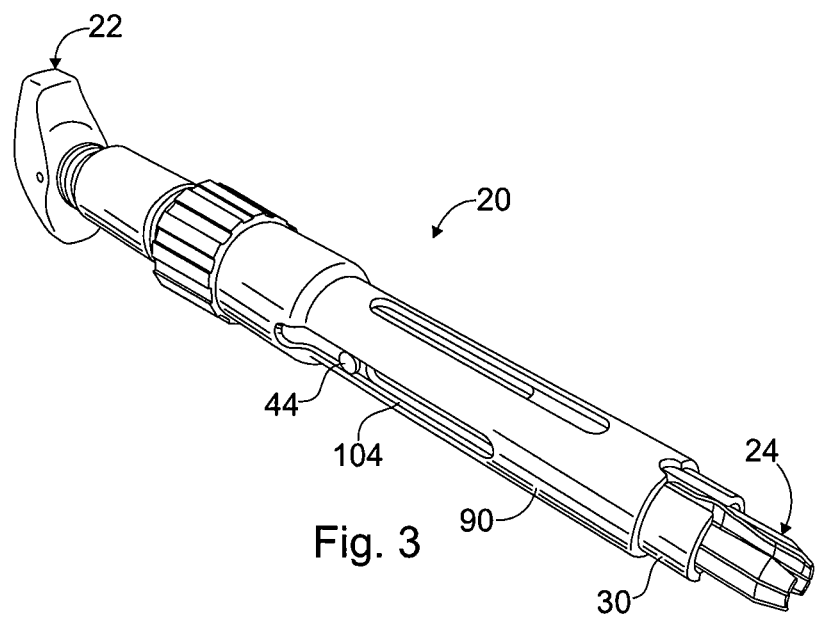
FIG. 3 is a second perspective view of the rod persuader embodiment of FIG. 1.
Figure 4:
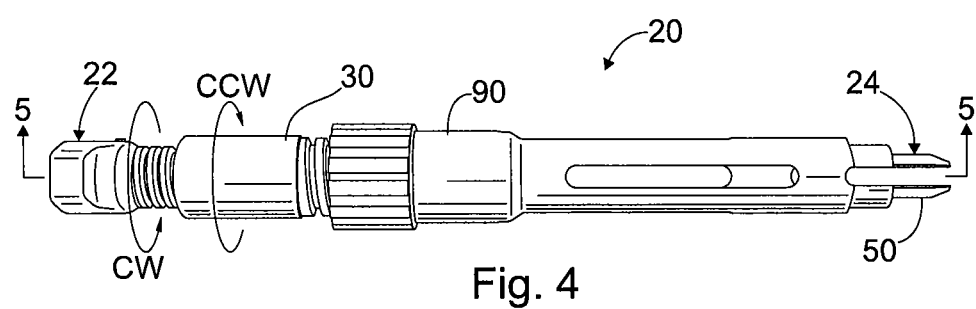
FIG. 4 is a second elevation view of the rod persuader embodiment of FIG. 1, rotated on its axis.

Aspects of the invention are illustrated and described herein with reference to specific embodiments. Nevertheless, the invention is not intended to be limited to the details shown. Rather, various modifications may be made in the details within the scope and range of equivalents of the claims and without departing from the invention.

Referring to the drawing figures generally, and to FIGS. 1-5 in particular, an exemplary rod persuader 20 in accordance with the present invention is shown. Rod persuader 20 includes a generally symmetrical design from its proximal end to its distal end, with components that assemble with one another to form a generally linear profile. The components of persuader 20 function in a two-step operation, which has the benefit of more precisely controlling the gripping of the implant, and the axial movement or "persuading" of the rod, each operation being lockable in any state, and each operation being independent from one another.

There has been a longstanding desire to simplify the operation of surgical instruments while at the same time increasing their functionality. Instruments that require multiple-step operations have generally been considered undesirable by device manufacturers and surgeons, to the extent that additional steps complicate the surgical procedure, and are less convenient than an instrument that combines multiple functions in a single step. As a result, there has been a push to develop instruments that carry out multiple functions in a single step. In these improved instruments, the motion of one component carries out multiple steps or functions simultaneously. In the rod persuader art, for example, devices have been manufactured which grip a screw implant and axially advance the rod simultaneously in a single manipulation of the instrument.

In a preferred embodiment of the invention which is counter-intuitive to the single step approach, the persuader 20 completely separates the implant gripping operation from the rod advancement operation, while still accomplishing both tasks in a single instrument. The separation of these steps works contrary to the desire of combining separate functions in a single operative step. Nevertheless, the separation of the gripping operation and the rod advancement operation in the persuader 20 has the unexpected benefit of working better than single-step devices. Gripping of the implant is more precisely controlled while the rod is axially advanced. Because gripping can be perfected independently of the rod being advanced, the gripping step is not compromised by simultaneous advancement of the rod, and vice versa. Accordingly, for example, the rod receiving body on the screw implant is not at risk of being clamped and squeezed too tightly while the rod is moved into the body, which can damage the screw implant. Conversely, there is no potential for the rod to be advanced into a rod receiving body that is not securely gripped. The gripping of the implant can be perfected with a very precise amount of force prior to advancing the rod, and the gripping forces do not change as the rod is advanced. Accordingly, the implant gripping step and the rod advancement step are each carefully controlled and are not influenced by one another.

As will be explained further, the separation of the gripping step from the advancement step allows incremental adjustments of either the gripping/clamping force or the rod position, at any time. Equally important, the separation of the two steps allows the persuader 20 to be compatible with a wider range of implant dimensions. That is, the tightening and loosening of the gripping end is controlled by a first component, while the axially advancement of the rod is controlled by a second component that moves independently from the first component. In this arrangement, the extent to which the gripping end can be tightened is not dependent on, or limited by, the range of axial motion available to the rod. All of the foregoing benefits will be more clearly visualized from the description below.

Rod persuader 20 includes a proximal end 22 that is manipulated by the user, and a distal end 24 for engagement with an implant. Rod persuader 20 includes a hollow tubular body 30, an inner shaft 50 extending through the interior of the body, and an outer shaft 90 that extends over a portion of the tubular body. Tubular body 30, inner shaft 50 and outer shaft 90 are coaxially arranged along a common axis and combine to form a narrow straight profile. Tubular body 30 includes a proximal end 32 positioned towards proximal end 22 of persuader 20, and a distal end 34 positioned towards distal end 24 of the persuader. Body 30 has a hollow bore 31 surrounded by an inner wall 36. Inner wall 36 includes a thread 40, shown best in FIG. 5, that cooperatively engages inner shaft 50 during an implant gripping procedure. Body 30 also includes an outer wall 38 having a thread 42 that cooperatively engages with outer shaft 90 during a rod advancement procedure.

Figure 6:
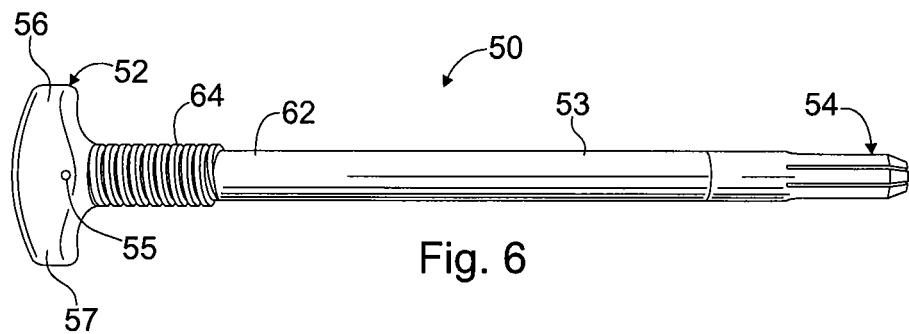
FIG. 6 is a first elevation view of an inner assembly of the rod persuader embodiment of FIG. 1.
Figure 7:
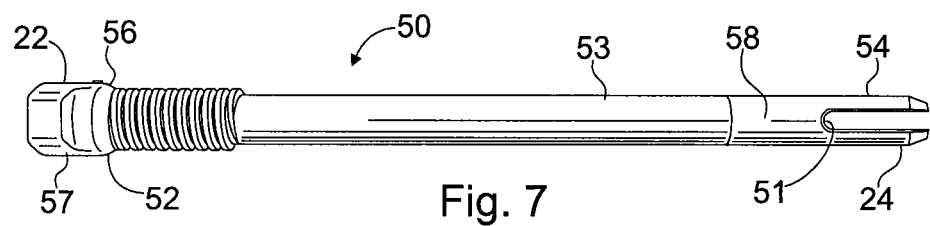
FIG. 7 is a second elevation view of the inner assembly shown in FIG. 6, rotated on its axis.
Figure 8:
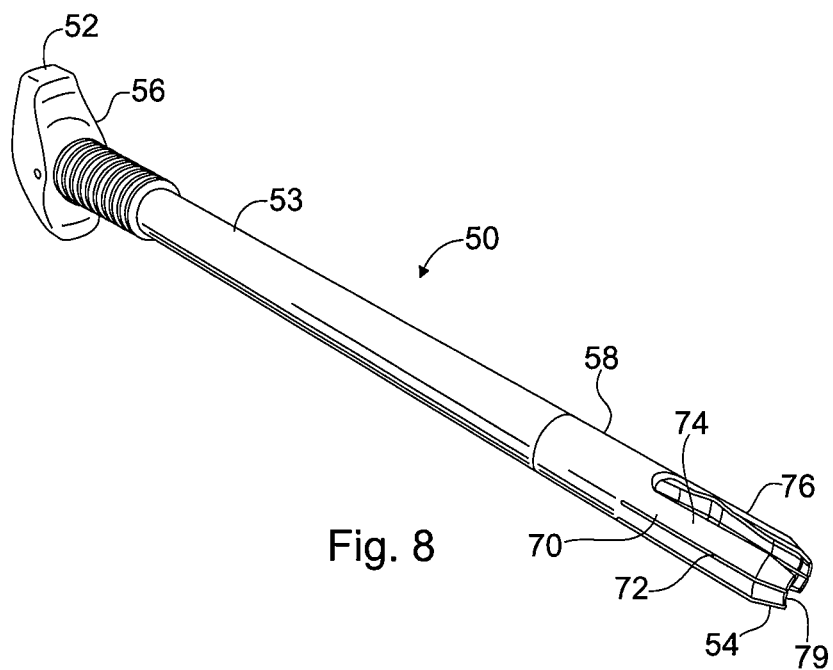
FIG. 8 is a perspective view of the inner assembly shown in FIG. 6.
Figure 9:
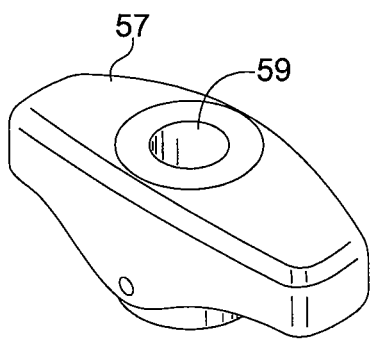
FIG. 9 is a perspective view of a first component of the inner assembly shown in FIG. 8.
Figure 10:
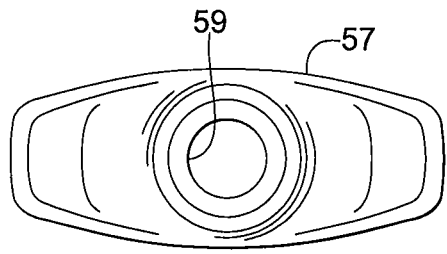
FIG. 10 is an end view of the first component of the inner assembly shown in FIG. 8.
Figure 11:
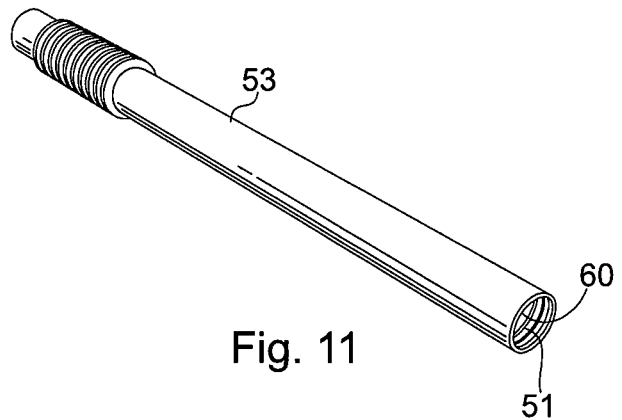
FIG. 11 is a perspective view of a second component of the inner assembly shown in FIG. 8.
Figure 12:
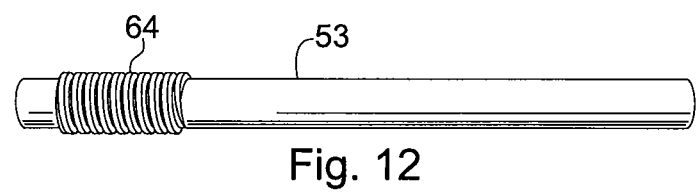
FIG. 12 is an elevation view of the second component of the inner assembly shown in FIG. 8.
Figure 13:
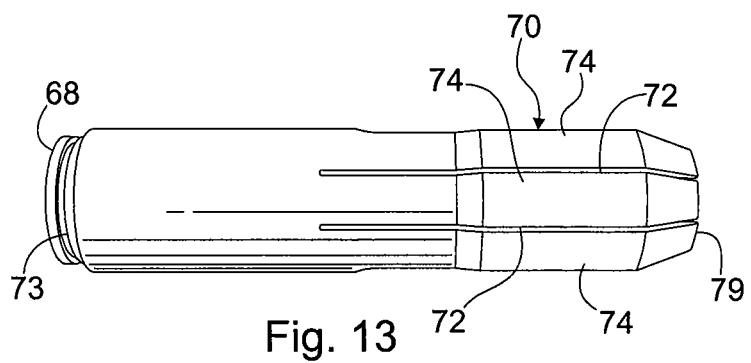
FIG. 13 is a first elevation view of a third component of the inner assembly shown in FIG. 8.

Referring now to FIGS. 5-16, inner shaft 50 includes a proximal end 52 that provides a control mechanism for gripping an implant, a central portion 53 and a distal end 54 that grips the implant. Proximal end 52 includes a handle portion 56 that may assume one of many configurations, including but not limited to a rounded knob, a loop handle or a circular disk extending in a plane that is normal to the longitudinal axis of the persuader 20. In FIG. 6, for example, handle portion 56 includes a T-bar 57 connected to a proximal portion of inner shaft 50. T-bar 57 is connected to the proximal portion of inner shaft 50 by a pin 55 that extends through the T-Bar. Handle portion 56 generally, and T-bar 57 in particular, is rotatable with respect to body portion 30 about the longitudinal axis of inner shaft 50.

An outer surface 62 of inner shaft 50 includes a thread 64 adjacent to handle portion 56. When the instrument is fully assembled, thread 64 on inner shaft 50 is axially positioned in overlapping proximity to thread 40 on the interior of body 30. The threads 64, 40 are configured to matingly engage with one another. In this arrangement, inner shaft 50 is axially advanceable relative to body 30 when the inner shaft rotates with respect to the body. The threads 64, 40 may be configured to cause axial displacement of inner shaft 50 relative to body 30 in response to a specific direction of rotation of T-bar 57. In the preferred embodiment, threads 64, 40 are configured such that handle portion 56 advances toward distal end 34 of body 30 ("distal displacement") in response to a clockwise direction of rotation, and advances away from distal end 34 of body 30 ("proximal displacement") in response to a counter-clockwise direction of rotation.

Inner shaft 50 has a hollow interior forming a bore 51. Bore 51 extends along the entire length of inner shaft 50, providing a generally linear conduit from the proximal end 22 of persuader 20 to the distal end 24. Handle portion 56 includes a cylindrical bore 59 that extends through the entire handle portion. Bore 59 forms part of bore 51 when inner shaft 50 is fully assembled. An inner surface 60 surrounds bore 51.

Distal end 54 of inner shaft 50 includes a gripping portion 58 for gripping an implant, as noted above. In a preferred embodiment, gripping portion includes a gripping end that is compatible with a wide variety of implant geometries and dimensions. In addition, gripping portion preferably has a geometry that allows the gripping portion to engage an implant, regardless of its axial orientation relative to the gripping portion. Persuader 20, as shown in the figures, includes a gripping portion 58 with a generally cylindrical collet 70. Collet 70 includes a plurality of annular slits 72 that extend through the wall of the inner shaft 50, forming a plurality of radially expandable branches 74. Branches 74 form a socket 76 having a mouth 79 at the distal end of inner shaft 50. Socket 76 and mouth 79 are adapted to axially receive an implant.

Collet 70 is preferably formed of a resilient flexible material. In the relaxed state, branches 74 are spread open and expanded radially outwardly. Branches 74 are biased toward the radially expanded position, in which the aggregate diameter of collet 70 is enlarged, and mouth 79 has a relatively large size. Inner bore 31 of body 31 has a diameter that is smaller than the diameter of collet 70 when branches 74 are radially expanded. In this arrangement, branches 74 are compressed radially inwardly by inner wall 36 of tubular body 30 and converge toward one another as collet 70 is retracted or moved proximally into the body. Conversely, branches 74 expand radially outwardly and away from one another under an outward bias when collet 70 is extended or advanced distally out of the tubular body 30.

A cylindrical collet, such as collet 70, has several advantages over forceps-style clamping elements and other gripping configurations that utilize two opposing plates to clamp an implant. First, a generally cylindrical shape provides a socket configuration that surrounds the whole perimeter of the screw implant. This maximizes surface contact with the exterior of the screw implant, providing a more secure clamp. Second, the generally cylindrical socket distributes the clamping force more evenly around the perimeter of the screw implant, rather than concentrating the clamping force on sides of the screw implant, which may alter the shape of the implant. Third, the stronger clamping effected by a generally cylindrical gripping end removes the need for tab/slot elements or other coupling elements to secure the connection between the instrument and the screw implant. Tab/slot elements and similar couplings require the surgeon to precisely align the orientation of the gripping end with the screw implant orientation, complicating the procedure. Tab/slot elements and couplings also limit the functionality of the instrumentation, as the instrument having the tab or slot can only be used with implants featuring the corresponding slot or tab, respectively. If modifications are made to such an implant, the instrument must also be modified. Instruments with specific coupling arrangements are not compatible with all implants, limiting their functionality.

Bore 51 extends into the interior of socket 76, and terminates at mouth 79. Branches 74 form a radially expandable wall 77 around bore 51. Bore 51 includes a variable-diameter section inside socket 76, as seen best in FIG. 5A. The diameter of bore 51 changes as it extends along the longitudinal axis of inner shaft 50 inside socket 76. In this configuration, inner surface 60 of bore 51 assumes a number of contour changes within the socket. The outer diameter of socket 76 is generally constant, while the inner diameter varies as a result of changes in the thickness of wall 77 along the socket. Wall 77 includes a relatively thick gripping section 80, along which the bore 51 has a constant diameter. In addition, wall 77 includes a thinned section 82. The thickness of wall 77 at thinned section 82 is substantially smaller than the thickness at the gripping section 80. A tapered section 84 extends between gripping section 80 and thinned section 82. Because of the difference in wall thickness between the gripping section 80 and thinned section 82, the flexibility of wall 77 at the thinned section is substantially greater than at the gripping section.

Figure 5:
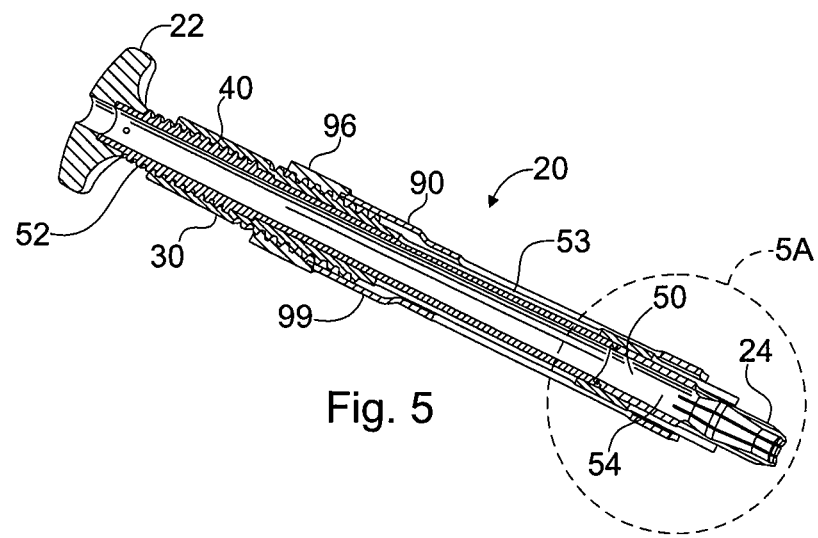
FIG. 5 is a cross sectional perspective view of the rod persuader embodiment of FIG. 1, taken through line 5-5 of FIG. 4.
Figure 5A:
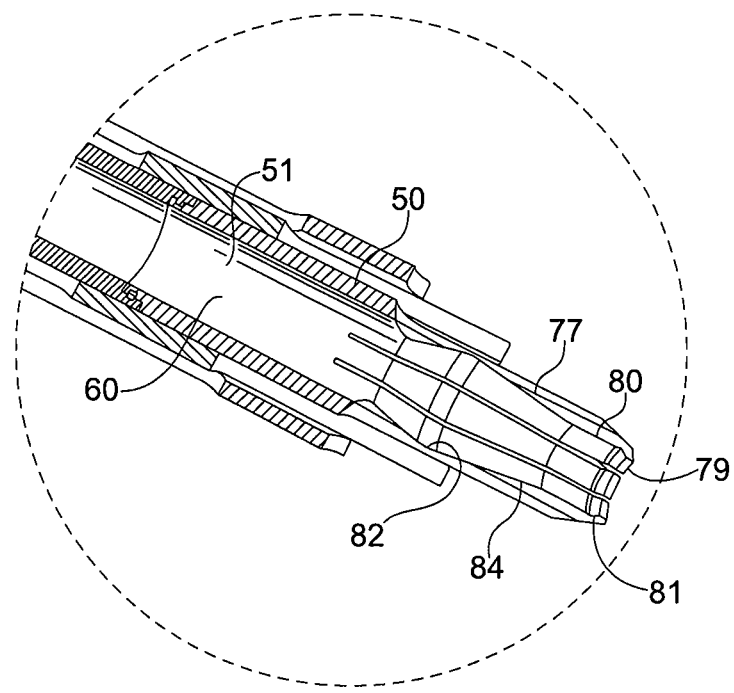
FIG. 5A is an enlarged detail view of the cross sectional perspective view of FIG. 5.
Figure 14:
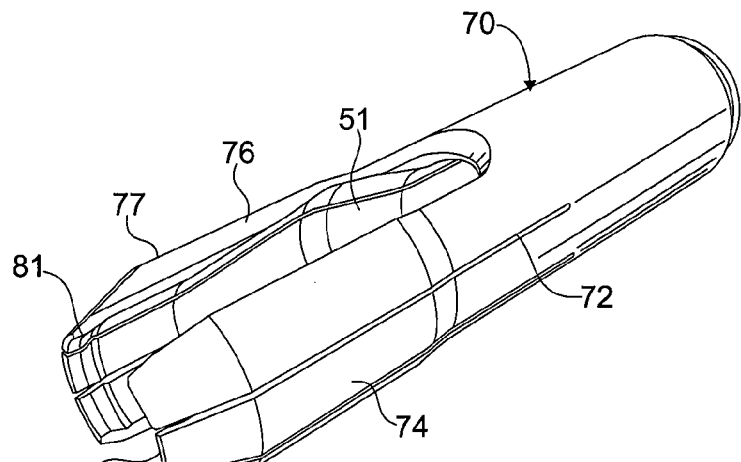
FIG. 14 is a perspective view of the third component of the inner assembly shown in FIG. 8.

Gripping section 80 is preferably compatible with a wide variety of implant sizes, shapes and configurations. A number of surface profiles are contemplated for this purpose. For example, gripping section 80 need not have a variable diameter throughout, and may form a constant-diameter bore section that extends from tapered section 84 to mouth 79. In this arrangement, gripping section 80 can engage and grip the exterior portions of a wide variety of hook and screw implants. This versatility is desirable, as noted above, if rod persuader 20 is being used to connect the rod to different sized implants. As an alternative, gripping section 80 may include a contour change to enhance the engagement between collet 70 and the hook or screw implant. Referring to FIGS. 5A and 14, for example, gripping section 80 includes a small ramp 81 that converges radially inwardly as it extends toward mouth 79. Ramp 81 may be used, for example, where a hook or screw implant has a similar contour on its exterior.

Figure 17:
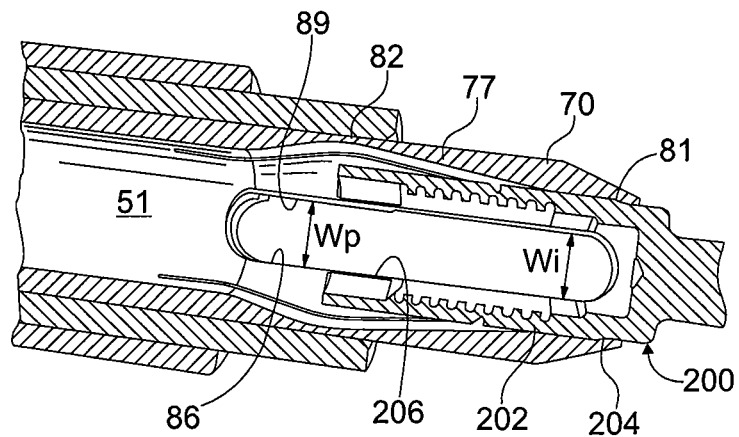
FIG. 17 is an enlarged cross-sectional perspective view of the rod persuader embodiment of FIG. 1 engaged with an implant, the rod persuader and implant being truncated for clarity.

Referring to FIG. 17, gripping portion 58 of persuader 20 is shown in engagement with a screw implant 200. Implant 200 includes a rod receiving body 202 that is partially inserted into socket 76. The exterior of body 202 is engaged by the gripping section 80 in socket 76. Body 202 is generally cylindrical and includes a change in diameter that forms a circumferential gripping ledge 204. Gripping ledge 204 forms a conical taper that angularly converges toward the longitudinal axis of the body 202. Annular ramp 81 has an angle of convergence with respect the longitudinal axis of inner shaft 50 which is equal or substantially equal to the angle of convergence of gripping ledge 204. As such, gripping section 80 conforms to the outer geometry of rod receiving body 202 at gripping ledge 204. Gripping ledge 204 abuts ramp 81 to act as a restraint that prevents axial slippage of rod receiving body 202 inside collet 70.

It should be noted that while ramp 81 enhances engagement with certain hook and screw implants, it is still versatile enough to accommodate different implant diameters, due to the radially expandable nature of collet 70. In addition, ramp 81 is symmetrical in a plane extending normal to the axis of persuader 20, and accommodates a number of detent configurations should they be used in lieu of a gripping ledge or other change of contour.

Figure 15:
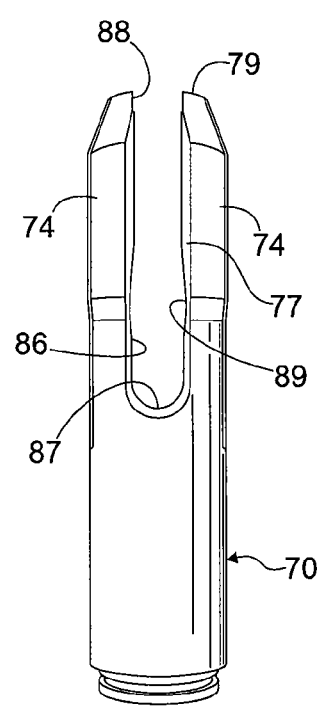
FIG. 15 is a second elevation view of a third component of the inner assembly shown in FIG. 8.
Figure 16:
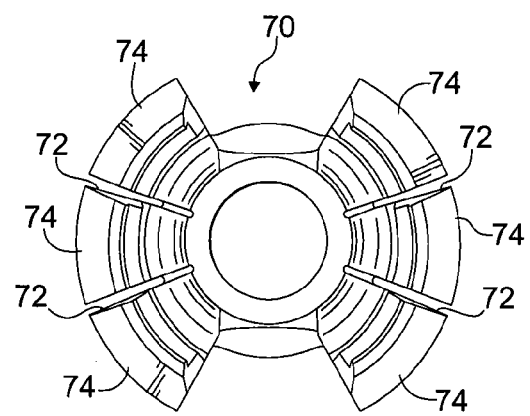
FIG. 16 is an end view of the third component of the inner assembly shown in FIG. 8.

Some of the branches 74 are partially cut to form a pair of diametrically opposed rod slots 86, as shown in FIG. 15. Rod slots 86 have an elongated U-shaped sidewall 87 forming a curved proximal end 87 and terminating at an open distal end 88 at mouth 79. The dimensions of rod slots 86 are sufficient to allow a rod member to be inserted through the slots in an orientation transverse to the axis of rod persuader 20, and allow translation of the rod member along the slots in a manner that will be described in more detail below. In this arrangement, the pair of rod slots 86 form a rod passage 89 for advancement of a rod. The dimensions of rod slots 86 are also adapted to cooperate with the many known hook or screw implants featuring top loading receiver bodies and opposing rod channels. In FIG. 17, for example, rod slots 86 align with a pair of diametrically opposed channels 206 on implant 200. The width "$W_p$" of each rod slot 86 on persuader 20 is generally equal to the width "$W_i$" of the corresponding channels 206 on implant 200. Alignment of rod slots 86 with channels 206 forms a closed rod passage between collet 70 and implant 200 for axial translation of a rod.

Figure 18:
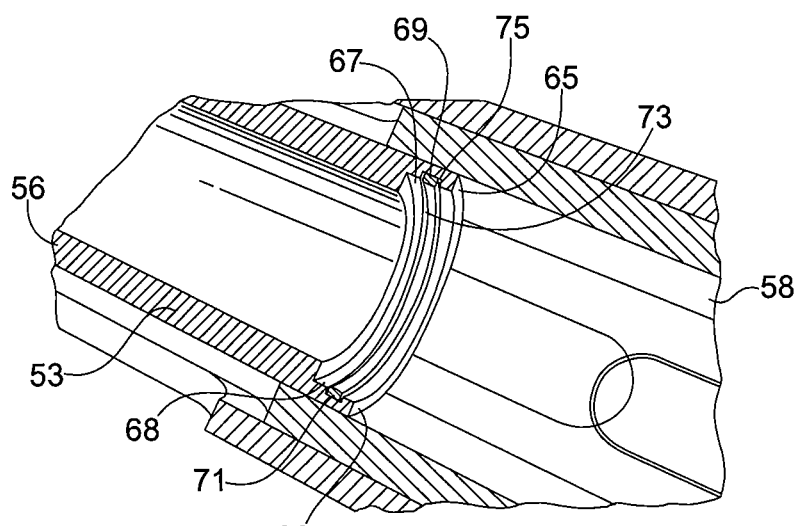
FIG. 18 is an enlarged cross-sectional perspective view of the rod persuader embodiment of FIG. 1, showing an exemplary coupling that interconnects components of the rod persuader.
Figure 19:
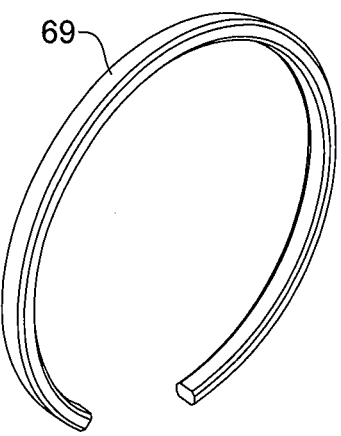
FIG. 19 is an enlarged perspective view of the coupling of FIG. 18.

Inner shaft 50 preferably includes a rotatable coupling between handle portion 56 and gripping portion 58 so that torque applied to the former is not transferred to the latter. A variety of configurations can be used to provide a rotatable coupling. Referring to FIG. 18, handle portion 56 has a distal end 65 with a female end 66. Gripping portion 58 has a proximal end 67 and a male end 68. Female end 67 and male end 68 interconnect in a sliding fit. Female end 67 includes an annular groove 71, and male end 68 includes a circumferential groove 73 that is arranged so as to align with annular groove on female end when the male end and female end are jointed together. Grooves 71, 73 form a circumferential cavity 75 that houses a snap ring 69. Snap ring 69, which is shown in more detail in FIG. 19, is preferably formed of a resilient elastic material that works as a bearing surface, allowing the handle portion 56 and gripping portion 58 to rotate relative to one another, while engaging the walls of cavity 75 to lock the handle and gripping portions together, preventing axial separation. In this arrangement, torque applied to T-bar 57 rotates handle portion 56 relative to body 30 to axially advance the entire inner shaft 50. Torque is not transferred to gripping portion 58, however, due to the sliding interfaces at snap ring 69. The gripping portion 58, and hence any rod or implant in engagement with the gripping portion, does not rotate in unison with handle portion 56. Inner shaft 50 can be axially advanced relative to body 30, with the handle portion 56 rotating relative to the body 30 and the orientation of the gripping portion 58 relative to the body remaining fixed. Therefore, proximal end 52 of inner shaft 50 is rotatable with respect to the implant, while the distal end 54 of inner shaft 50, particularly collet 70, is restrained against rotation.

Figure 20:
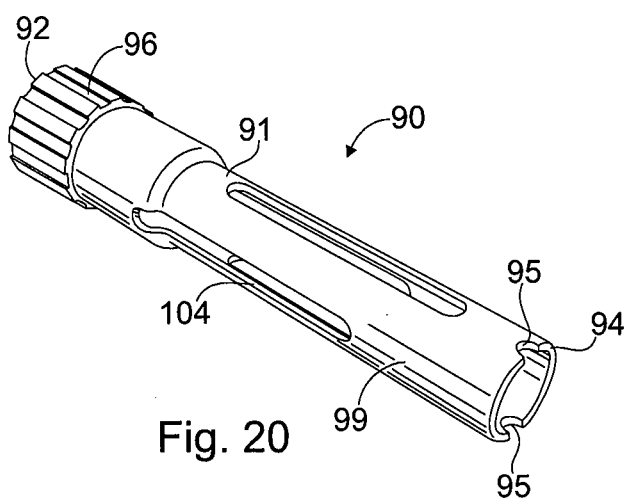
FIG. 20 is an enlarged perspective view of an outer assembly of the rod persuader embodiment of FIG. 1.
Figure 21:
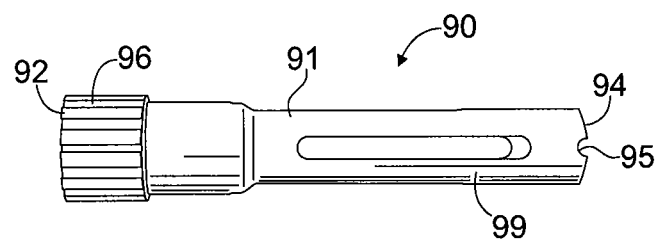
FIG. 21 is a first elevation view of the outer assembly of FIG. 20.
Figure 22:
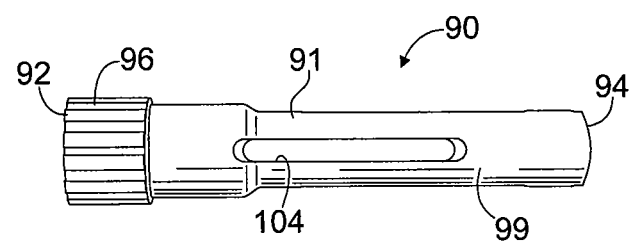
FIG. 22 is a second elevation view of the outer assembly of FIG. 20, rotated on its axis.
Figure 23:
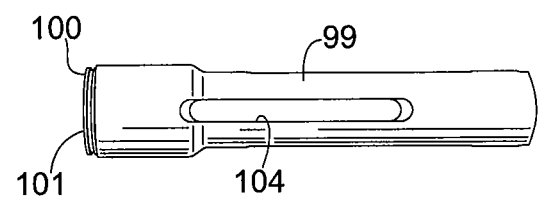
FIG. 23 is an elevation view of a first component of the outer assembly of FIG. 20.
Figure 24:
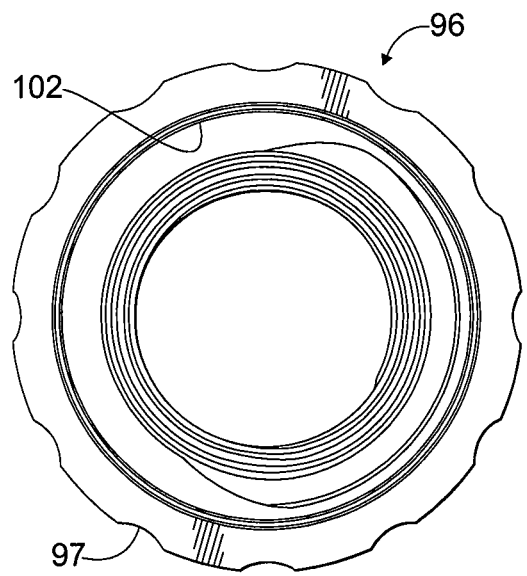
FIG. 24 is an enlarged end view of a second component of the outer assembly of FIG. 20.
Figure 25:
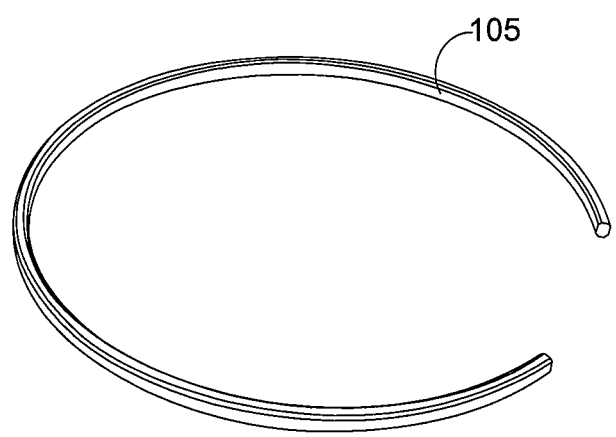
FIG. 25 is an enlarged perspective view of a coupling that interconnects components of the outer assembly of FIG. 20.

Referring now to FIGS. 20-22, outer shaft 90 has a generally cylindrical body 91 adapted to surround the exterior of body 30 in coaxial alignment. Outer shaft 90 is operable to advance a rod into the rod receiving portion of a hook or screw implant, once the hook or screw implant is secured in the gripping portion of inner shaft 58. A proximal end 92 of outer shaft 90 cooperatively engages body 30 to adjust the axial position of the outer shaft relative to the body and inner shaft 50. A distal end 94 of outer shaft 90 engages and carries a rod to be positioned within the rod receiving body of an implant. Distal end 94 includes a pair of diametrically opposed notches 95, each having a generally circular curvature. The curvature of notches 95 are preferably adapted to conform to the curvature of the rod to be contacted by outer shaft 90.

In a preferred embodiment, outer shaft includes a main component for advancing the rod, and an adjustment component for controlling the position of the main component. Referring to FIGS. 20-22, outer shaft 90 includes an adjustment knob 96 and a persuader member 99. Adjustment knob 96 is displaceable with respect to body 30 to adjust the position of a rod. More specifically, adjustment knob 96 cooperatively engages body 30 to provide a controlled displacement of a rod, the position of the rod being lockable at any time and at any position within the rod passage 89 in collet 70. Referring now to FIGS. 23-26, persuader member 99 includes a proximal end 100 with a circumferential flange 101. Knob 96 includes a corresponding annular groove 102 that receives the circumferential flange 101. Flange 101 slidably engages the bottom of groove 102, forming a rotatable connection between knob 96 and persuader member 99. Knob 96 and persuader member 99 are locked together in a rotatable manner by a snap ring 105 that is similar to the snap ring used to interconnect the handle portion 56 and gripping portion 58 of inner shaft 50. Snap ring 105 is shown in more detail in FIG. 25. In this rotatable coupling arrangement, knob 96 is rotatable relative to persuader member 99, but in an axially fixed position relative to the persuader member.

Figure 26:
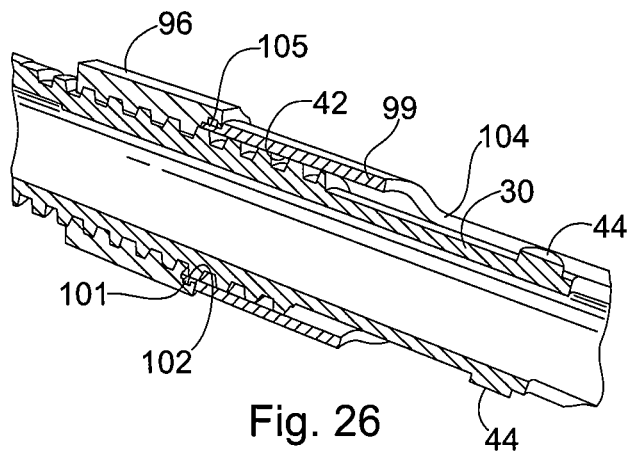
FIG. 26 is an enlarged cross-sectional perspective view of the rod persuader embodiment of FIG. 1, showing the cooperation between components, wherein the components are truncated for clarity.
Figure 27:
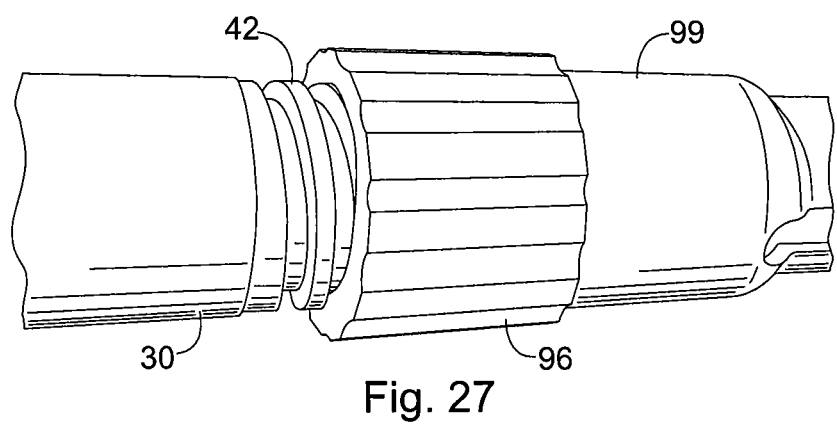
FIG. 27 is an enlarged perspective view of the rod persuader embodiment of FIG. 1, showing the cooperation between components, wherein the components are truncated for clarity.

Knob 96 is rotatable to axially displace outer shaft 90 relative to body 30. A knurled or grooved exterior 97 on knob 96 assists with gripping the knob. As with inner shaft 50, outer shaft 90 is axially displaceable relative to body 30 in a manner that allows precise axial positioning of a rod. Referring now to FIGS. 26 and 27, knob 96 includes an internal thread 103 that cooperatively engages outer thread 42 on the exterior of body 30. Knob 96 is axially displaceable relative to body 30 in response to rotation of the knob. As knob 96 is rotated in first direction, knob 96 is displaced axially with respect to body 30 toward the proximal end 22 of persuader 20. This displacement of knob 96 exerts a pulling force on the proximal end of persuader member 99, moving the persuader member toward proximal end 22 of persuader 20. When knob 96 is rotated in a second direction, knob 96 is displaced axially with respect to body 30 toward distal end 24 of persuader 20. This displacement of knob 96 exerts a pushing force on the proximal end of persuader member 99, moving the persuader member toward distal end 24 of persuader 20. Proximal end 100 of persuader member 99 has an enlarged diameter and a corresponding enlarged bore section so that the inner wall of the persuader member is positioned radially outwardly from the outermost edges of external thread 42 on body 30. In this arrangement, persuader member 99 passes axially over body 30 without engagement with or interference from thread 42. Thread 42 extends along a sufficient portion of body 30 that corresponds with the axial distance of travel of a rod during placement of the rod.

Figure 28:
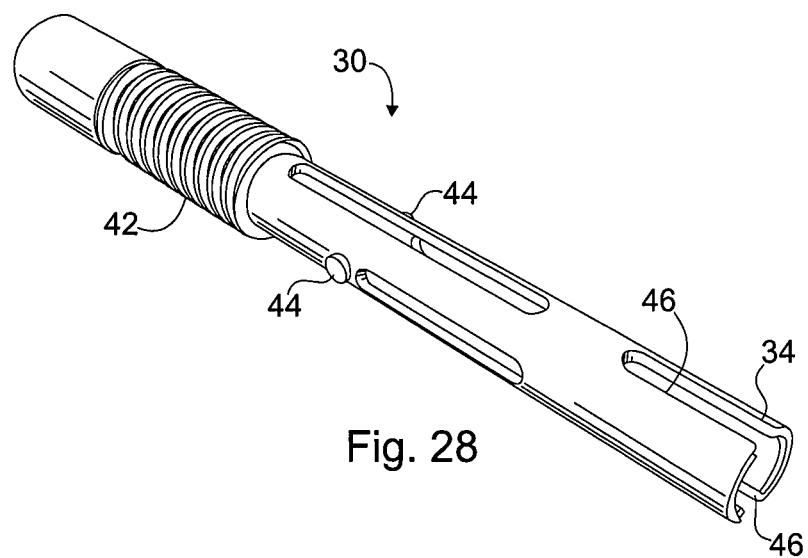
FIG. 28 is a perspective view of a body portion of the rod persuader embodiment of FIG. 1.
Figure 29:
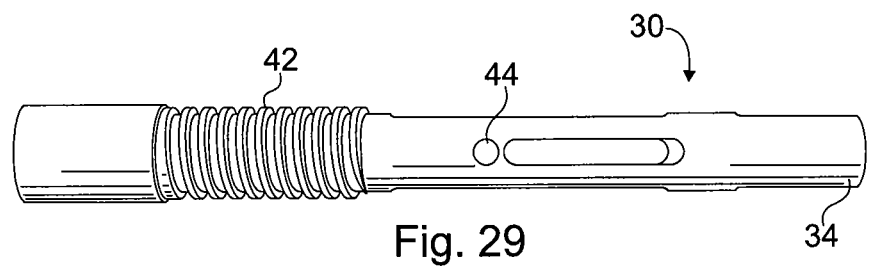
FIG. 29 is a first elevation view of the body portion of FIG. 28.
Figure 30:
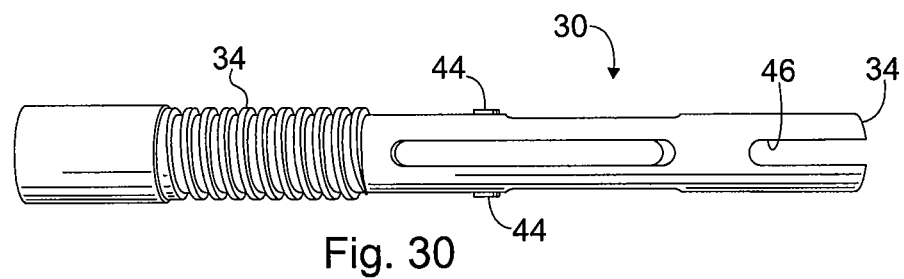
FIG. 30 is a second elevation view of the body portion of FIG. 28, rotated on its axis.
Figure 31:
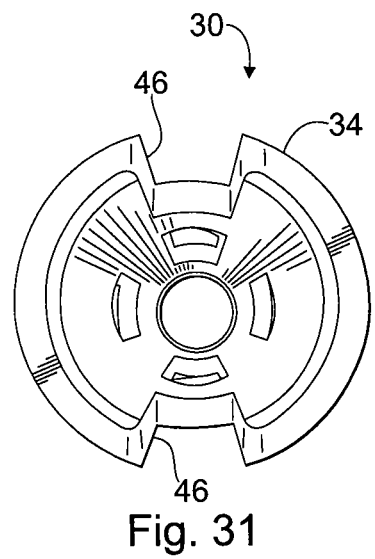
FIG. 31 is an end view of the body portion of FIG. 28.

Referring now to FIGS. 28-31, tubular body 30 is shown in more detail. Distal end 34 includes a pair of diametrically opposed slots 46. Slots 46 are arranged so as to align with rod slots 86 on inner shaft 50 when the inner shaft is positioned in body 30. Body 30 and outer shaft 90 preferably include one or more alignment surfaces to maintain slots 46 in alignment with rounded notches 95 at distal end 94 of the outer shaft. This ensures that that a rod being carried by persuader member 99 is aligned with slots 46, allowing advancement of the rod through body 30. Referring to FIG. 28, the alignment surfaces on body 30 are in the form of a pair of bosses 44 that project radially outwardly from a midportion of the body. A pair of longitudinal alignment slots 104 in persuader member 99, which are best visualized in FIGS. 1-3, receive the bosses 44 and restrict or substantially prevent rotational displacement of body 30 relative to outer shaft 90.

One method of operation of the rod persuader embodiment 20 will now be described in detail, in accordance with the present invention. A bone implant with a rod receiving body is implanted into the vertebra, and a rod is positioned in proximity to the rod receiving channel. The rod may be in one of several positions relative to the seat of the rod receiving body. Rod persuader 20 is prepared for the procedure by adjusting collet 70 to a relatively open condition. In the relatively open condition, branches 74 are radially expanded in their relaxed state, increasing the size of mouth 79 to provide a sufficiently large opening to receive the implant. The size of mouth 79 is controlled by adjusting the relative position of collet 70 with respect to the distal end 34 of tubular body 30. To adjust collet 70 to the relatively open condition, the collet is extended distally out of the body so as to remove any radial compression from branches 74. To this end, T-bar 57 is rotated in a clockwise direction, represented by curved arrow "CW" in FIG. 4. As T-bar 54 is rotated in the clockwise direction, outer thread 64 on inner shaft 70 rotates clockwise and engages inner thread 40. The rotational engagement between threads 40, 64 drives handle portion 56 of inner shaft 50 into body 30. Handle portion 56 exerts axial force on gripping portion 58 through snap ring coupling 69. Torque is not transferred from handle portion 56 to gripping portion 58, however. As a result, gripping portion 58 is displaced in a distal direction relative to body 30, without rotating. The relative orientation of gripping portion 58, and consequently collet 70, remains substantially fixed.

Once collet 70 is extended to the relatively open condition, the first stage of securing the persuader 20 to the implant begins. Collet 70 is lowered down over the rod and the implant. Rod slots 86 of collet 70 are aligned over the rod so that the rod passage 89 is generally parallel to the rod's orientation, allowing the rod to enter into the rod slots. Because collet 70 is generally cylindrical, the mouth is generally circular, and the collet can lower down over the implant without regard to the relative orientation of the implant.

Collet 70 is then carefully tightened over the implant to secure rod persuader 20 to the implant. To tighten collet 70, T-bar 57 on handle portion 56 of inner shaft 50 is rotated counter-clockwise, as represented by curved arrow "CCW" in FIG. 4. Counter-clockwise rotation of T-bar retracts collet 70 into tubular body 30, gradually compressing branches 74 against their outward bias so as to tighten the grip around the implant. Those skilled in the art will appreciate that many implants are constructed of thin deformable materials. Many such implants have cylindrical rod receiving portions with inner threads that must maintain their cylindrical shape in order to properly mate with set screws or other round anchors. The threaded engagement between inner shaft 50 and body 30 provides an inclined ramp that allows gradual and controlled axial displacement of collet 70, such that compression forces on the implant are very gradually introduced. Once sufficient gripping pressure is applied onto the implant, as determined by the user, rotation of T-bar 57 is halted. In the preferred embodiment, substantial frictional resistance between threads 40 and 64 stabilizes the relative position of inner shaft in a locked condition with respect to body 30. The threaded engagement provides an infinite number of positional adjustments to provide a precise amount of pressure on the implant without exerting too much pressure.

With the rod persuader 20 firmly secured to the implant, the second stage, i.e. advancing the rod, begins. At this stage, the rod extends through the rod slots 86 of inner shaft 56. To advance the rod, outer shaft 90 is displaced distally relative to body 30 and inner shaft 50, the body and inner shaft being relatively fixed in position. Adjustment knob 96 is rotated in a clockwise direction, which as noted above is represented by curved arrow "CW" in FIG. 4. As knob 96 is rotated, inner thread 103 engages outer thread 42 on body 30 to drive the knob distally toward the rod and collet 70. As knob 96 is driven in the distal direction, the knob exerts axial force on persuader member 99 through snap ring coupling 105, without imparting torque to the persuader member. As such, persuader member 99 is driven in the distal direction as the knob is displaced distally, but the persuader member does not rotate. Rounded notches 95 on persuader member 99 are aligned with slots 44 on body 30, and are maintained in alignment by the engagement between bosses 44 and alignment slots 104. Persuader member 99 may be advanced distally into contact with the rod, at which time the rounded notches 95 capture the rounded contour of the rod. Knob 97 is rotated until the rounded notches advance the rod into a desired position in the rod receiving body of the implant.

It will be noted that the first stage of securing the implant and the second stage of advancing the rod occur entirely independent of one another. It is conceivable that the first stage can be done before, during or after the second stage. Advancement of the rod does not affect the engagement between collet 70 and implant. In particular, advancing the rod does not further tighten the engagement of the branches 74 around the implant or exert any additional pressure on the implant. The implant gripping function is completely isolated from the rod advancement function, so that either function can be started or stopped at any time.

Once the rod is set in the desired position in the second stage, a locking mechanism is introduced through rod persuader 20 while the rod persuader is engaged with the implant. Bore 51 of inner shaft 50 is adapted to receive a locking element and insertion tool, so that the rod can be secured with, the locking element without releasing and removing rod persuader 20. For example, where the implant is adapted to receive a set screw locking mechanism, the set screw can be inserted down through rod persuader 20 and into the rod receiving body of the implant. The set screw could be mounted on the distal end of a driver tool, and the tool can be inserted into bore 51. The driver tool can then be operated through bore 51 to tighten the set screw into the implant above the rod, locking the position of the rod. The insertion tool may be a hex head screw driver, flat head screw driver, or other tool.

Once the set screw is in place, the insertion tool is removed from bore 51, and rod persuader 20 is released from the implant. Rod persuader 20 is released by rotating T-bar 57 clockwise. Clockwise rotation of T-bar displaces the collet 70 distally with respect to distal end 34 of body 30, so that branches 74 extend outside of body 30. Compressive force on branches 74 is thereby released or reduced, allowing the branches to expand radially outwardly under the spring bias in the collet. As a result, the branches release their grip on the implant. Continued clockwise rotation of T-bar 57 increases the diameter of mouth 79 until the size of the mouth opening provides sufficient clearance to allow removal of the collet 70 from the implant.

Figure 32:
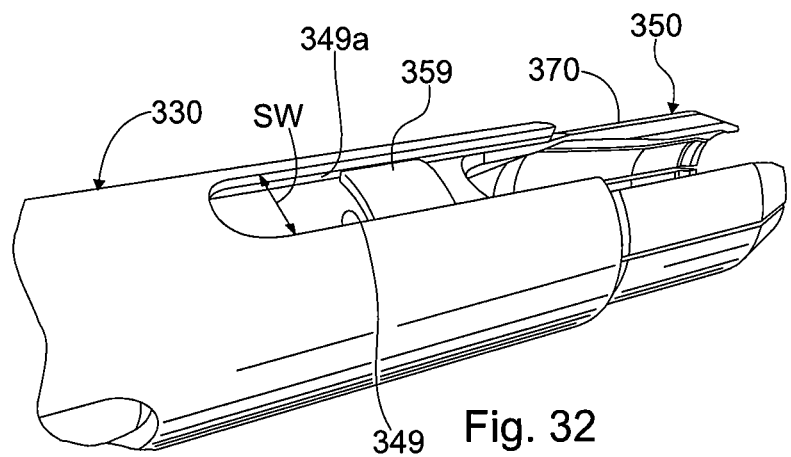
FIG. 32 is a truncated perspective view of components that comprise an alternate embodiment of the rod persuader in accordance with the invention.

In a preferred embodiment, rotation of the gripping portion of the inner shaft relative to the tubular body is substantially limited or prevented. Referring now to FIG. 32, alternate exemplary components are shown, specifically an alternate tubular body 330 and an inner shaft 350. Tubular body 330 includes a U-shaped slot 349 having a slot width "SW". Slot 349 is open at the distal end of the tubular body. Inner shaft 350 includes a rectangular boss 359 arranged in slot 349. A pair of opposing sliding surfaces 349a beneath the slot opening engage or abut the corresponding sides of boss 359. In this arrangement, inner shaft 350 is permitted to move axially with respect to tubular body 330, but has a very limited capacity to rotate about its longitudinal axis relative to the tubular body due to the confinement of boss 359 in slot 349. Depending on the amount of clearance between boss 359 and sliding surfaces 349a, the rotation can be substantially prevented or limited within a small range rotation if desired.

In some instances, it may be desirable to supply a torque on the rod persuader to oppose torque being applied during manipulation of the persuader. For example, it may desirable to apply an opposing torque during rotation of the adjustment knob, for example. By supplying an opposing torque or "counter-torque" on the persuader, the persuader is not subject to substantial rotation or twisting, transferring zero net torque to the implant that is gripped by the persuader. A number of gripping surfaces may be provided on the rod persuader to assist in securing a counter-torque implement to the rod persuader.

Figure 33:
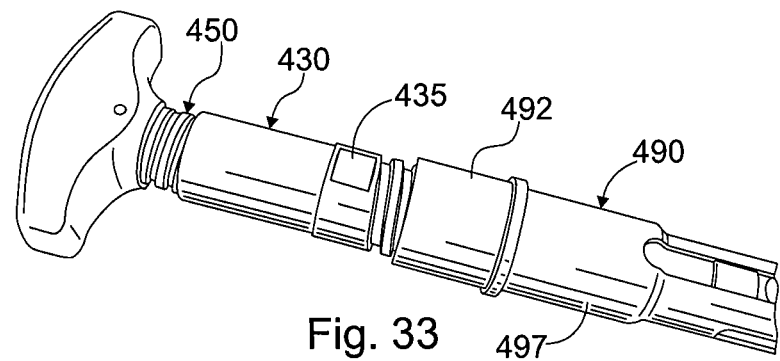
FIG. 33 is a truncated perspective view of components that comprise another alternate embodiment of the rod persuader in accordance with the invention.
Figure 34:
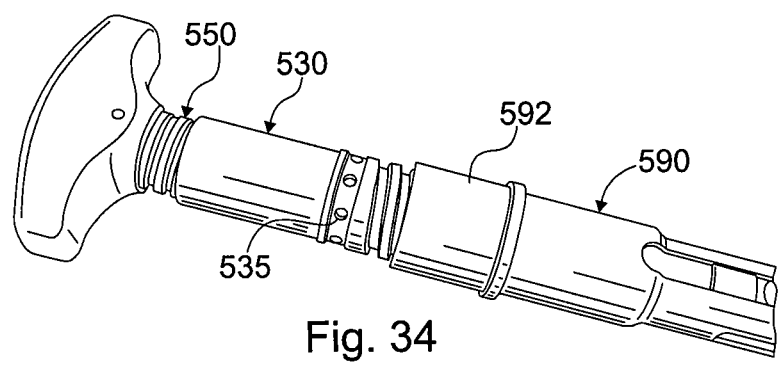
FIG. 34 is a truncated perspective view of components that comprise another alternate embodiment of the rod persuader in accordance with the invention.

Referring to FIG. 33, an alternate rod persuader embodiment includes an inner shaft 450, a tubular body 430 and an outer shaft 490. Outer shaft 490 includes an adjustment knob 492 and a persuader member 497, similar to components described above. A pair of diametrically opposed flattened surfaces 435 are provided on the outer circumference of tubular body 430 to provide an engagement surface for a counter-torque tool, including but not limited to a crescent wrench, for example. Another alternate rod persuader embodiment is shown in FIG. 34. This embodiment has an inner shaft 550, a tubular body 530 and an outer shaft 590 with adjustment knob 592. Tubular body 530 includes a number small gripping holes 535 incrementally spaced around the circumference of the tubular body. Gripping holes 535 are configured for engagement with a spanner-style wrench to apply a counter-torque to tubular body 530.

It should be noted that the above-described gripping surfaces are only two examples of surfaces that can be added for engagement with a counter-torque implement. A number of other gripping surfaces may be used in accordance with the invention. Moreover, the gripping surfaces need not be on the tubular body but may be on the outer shaft or another component to provide a balancing counter-torque.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A rod persuader assembly comprising:
   a tubular body having a proximal end and a distal end opposite the proximal end;
   an inner shaft disposed within the tubular body and axially displaceable relative to the tubular body, the inner shaft having a gripping mechanism disposed at a distal end of the inner shaft, a handle mechanism disposed at a proximal end of the inner shaft that is opposite the distal end of the inner shaft, and a longitudinal axis extending from the distal end of the inner shaft to the proximal end of the inner shaft,
   wherein the tubular body includes at least one boss extending away from an outer surface of the tubular body; and
   an outer shaft axially displaceable relative to the tubular body, the outer shaft having a proximal end, a distal end opposite the proximal end of the outer shaft, and a closed slot defined therein and located intermediate the proximal and distal ends of the outer shaft,
   wherein the tubular body and the inner shaft are disposed within the outer shaft, the at least one boss of the tubular body extending through the closed slot of the outer shaft, the proximal end of the tubular body and the proximal end of the inner shaft extend beyond the proximal end of the outer shaft, and the distal end of the tubular body and the distal end of the inner shaft extend beyond the distal end of the outer shaft,
   wherein the gripping mechanism comprises a collet having a plurality of branches radially displaceable relative to the longitudinal axis of the inner shaft between an open position and a closed position through rotation of the handle mechanism relative to the tubular body about the longitudinal axis of the inner shaft, and
   wherein the proximal end of the inner shaft is separate and distinct from the distal end of the inner shaft and is rotatably coupled to the distal end of the inner shaft, the proximal end of the inner shaft being rotatable independently of the distal end of the inner shaft.

2. The rod persuader assembly of claim 1, wherein the proximal end of the inner shaft is rotatably coupled to the distal end of the inner shaft by a first snap ring disposed therebetween.

3. The rod persuader assembly of claim 2, wherein the first snap ring is configured to facilitate axial movement of the inner shaft relative to the tubular body and prevent transfer of torque from the proximal end of the inner shaft to the distal end of the inner shaft when the handle mechanism is rotated.

4. The rod persuader assembly of claim 3, wherein the gripping mechanism includes a first end and a second end opposite the first end, the second end of the gripping mechanism includes the collet, and the inner shaft further includes a connection mechanism which is configured to interconnect with the first end of the gripping mechanism.

5. The rod persuader assembly of claim 4, wherein the interconnection of the connection mechanism and the first end of the gripping mechanism is configured to be a sliding fit.

6. The rod persuader assembly of claim 4, wherein the connection mechanism and the first end of the gripping mechanism each comprise annular grooves that define a cavity in which the first snap ring is housed.

7. The rod persuader assembly of claim 1, wherein the tubular body further includes an inner thread and the inner shaft includes an outer thread which overlaps and matingly engages the outer thread of the inner shaft.

8. The rod persuader assembly according to claim 7, wherein the outer shaft comprises an adjustment knob rotatably connected to a persuader member.

9. The rod persuader assembly according to claim 8, wherein the adjustment knob is connected to the persuader member by a second snap ring disposed therebetween.

10. The rod persuader assembly according to claim 9, wherein the second snap ring is configured to facilitate rotation of the adjustment knob relative to the persuader member and axially fix a position of the adjustment knob relative to the persuader member.

11. The rod persuader assembly according to claim 9, wherein the adjustment knob and the persuader member each comprise annular grooves that define a second cavity in which the second snap ring is housed.

12. The rod persuader assembly according to claim 8, wherein the tubular body further includes an outer thread and the adjustment knob includes an inner thread which overlaps and matingly engages the outer thread of the tubular body.

13. The rod persuader assembly according to claim 12, wherein an inner diameter of the persuader member is greater than an outer diameter of the tubular body, and wherein rotation of the adjustment knob axially displaces the outer shaft relative to the tubular body and the persuader member axially passes over the tubular body free of contacting the outer surface of the tubular body.

14. The rod persuader assembly of claim 1, wherein the distal end of the inner shaft further includes a plurality of slits extending through a wall of the inner shaft and forming the plurality of branches.

15. The rod persuader assembly according to claim 1, wherein the plurality of branches form a socket defining a mouth configured to receive an implant.

16. The rod persuader assembly according to claim 15, wherein the inner shaft further comprises a hollow interior forming a bore extending along an entire length of the longitudinal axis, the bore extending into an interior of the socket, and wherein the plurality of branches define a radially expandable wall around the bore.

17. The rod persuader assembly according to claim 16, wherein the bore includes a variable diameter section within the socket.

18. The rod persuader assembly according to claim 1, wherein the plurality of branches include a first set of branches opposing a second set of branches separated from the first set of branches by a U-shaped sidewall.

19. The rod persuader assembly according to claim 1, wherein the distal end of the outer shaft comprises a pair of opposing curved notches defined therein.

20. The rod persuader assembly according to claim 1, wherein the distal end of the inner shaft comprises a pair of opposing open ended rod slots defined therein, the distal end of the tubular body comprises a pair of opposing open ended alignment slots defined therein, the alignment slots of the tubular body being in alignment with the rod slots of the inner shaft when the inner shaft is disposed within the tubular body.

21. The rod persuader assembly according to claim 1, wherein the inner shaft further comprises a boss extending away from an outer surface of the inner shaft, the distal end of the tubular body further comprises an open ended slot defined therein, the boss of the inner shaft being in sliding engagement with sliding surfaces formed beneath the open ended slot of the tubular body.

22. The rod persuader assembly according to claim 1, further comprising a pair of diametrically opposed flattened surfaces provided on the outer surface of the tubular body, the flattened surfaces being disposed intermediate the proximal end of the tubular body and the distal end of the tubular body relative to the longitudinal axis of the inner shaft.

23. The rod persuader assembly according to claim 1, further comprising a plurality of gripping apertures defined in the outer surface of the tubular body, the plurality of gripping apertures being disposed around a circumference of the tubular body and located intermediate the proximal end of the tubular body and the distal end of the tubular body relative to the longitudinal axis of the inner shaft.

\* \* \* \* \*